United States Patent
Nishikiori et al.

(10) Patent No.: US 6,246,786 B1
(45) Date of Patent: *Jun. 12, 2001

(54) PARTICLE ANALYZER

(75) Inventors: Mizuho Nishikiori; Shinichi Nishida, both of Kobe (JP)

(73) Assignee: SYSMEX Corporation, Hyoto (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/932,601

(22) Filed: Sep. 17, 1997

(30) Foreign Application Priority Data

Sep. 19, 1996 (JP) .................................................. 8-247587

(51) Int. Cl.[7] .............................. G06K 9/00; G01N 33/48
(52) U.S. Cl. ................................ 382/134; 356/39; 436/63
(58) Field of Search .................................. 382/128, 133, 382/134; 356/39, 73; 436/63

(56) References Cited

U.S. PATENT DOCUMENTS

| 3,502,974 | * | 3/1970 | Coulter et al. . | |
|---|---|---|---|---|
| 3,549,994 | * | 12/1970 | Rothermel et al. . | |
| 4,485,175 | * | 11/1984 | Ledis et al. | 436/63 |
| 4,661,913 | * | 4/1987 | Wu et al. | 382/133 |
| 5,018,209 | * | 5/1991 | Bacus et al. | 382/133 |
| 5,125,737 | * | 6/1992 | Rodriguez et al. | 356/39 |
| 5,134,662 | * | 7/1992 | Bacus et al. | 382/133 |
| 5,155,044 | * | 10/1992 | Ledis et al. | 436/17 |
| 5,260,192 | * | 11/1993 | Russell et al. | 356/39 |
| 5,299,118 | * | 3/1994 | Martens et al. | 600/509 |
| 5,426,499 | * | 6/1995 | Kosaka et al. | 356/39 |
| 5,436,978 | * | 7/1995 | Kasdan | 382/133 |
| 5,532,943 | * | 7/1996 | Asano et al. | 382/133 |
| 5,555,198 | * | 9/1996 | Asano | 382/128 |
| 5,721,433 | * | 2/1998 | Kosaka | 382/133 |
| 5,731,206 | * | 3/1998 | Ledis et al. | 436/17 |
| 5,735,274 | * | 4/1998 | Shibata et al. | 600/309 |
| 5,757,476 | * | 5/1998 | Nakamoto et al. | 356/73 |
| 5,790,308 | * | 8/1998 | Kamentsky | 359/393 |
| 6,006,140 | * | 12/1999 | Carter | 700/56 |

FOREIGN PATENT DOCUMENTS 7-85168    3/1995   (JP) .

* cited by examiner

Primary Examiner—Amelia M. Au
Assistant Examiner—Mehrdad Dastouri (57) ABSTRACT

A particle analyzer includes a detection section to detect a parameter representative of characteristics of particles in a sample, a processing section to process the detected parameter, and an output section to output a result obtained by the processing section, wherein the processing section includes a distribution diagram producing section to produce a distribution diagram based on the parameter detected by the detection section, an area storing section to store a predetermined reference pattern beforehand, and a control section to permit the output section to output the reference pattern in addition to the distribution diagram.

14 Claims, 13 Drawing Sheets

PARTICLE ANALYZER

This application is related to Japanese application No. Hei 8(1996)-247587, filed on Sept. 19, 1996 whose priority is claimed under 35 U.S.C. Section 119, the disclosure of which is incorporated by reference in its entirety.

BACKGROUND OF THE INVENTION

1. Field of the Invention

The present invention relates to a particle analyzer for measuring the number and characteristics of particles to be analyzed, for example, blood cells, in a liquid sample. The present invention provides a particle analyzer for allowing a user to intuitively judge the characteristics of particles from the scattergram thereof.

2. Description of Related Art

Conventional particle analyzers of this type count the number of various kinds of cells in blood samples such as erythrocytes, leukocytes, platelets and the like, and at the same time, electrically or optically measure parameters representative of characteristics of the cells to produce and display distribution diagrams such as a one-dimensional frequency distribution diagram and a two-dimensional scattergram for analyzing the cells based on the measured parameters [see, for example, Japanese Unexamined Patent Publication (Kokai) No. Hei 7(1995)-85168].

With the conventional particle analyzers, however, it is not easy and therefore requires considerable experience for a user to judge from the displayed distribution diagram whether a distribution state is normal or abnormal.

SUMMARY OF THE INVENTION

In view of the above-mentioned circumstances, an object of the present invention is to provide a particle analyzer to enable a user to judge a distribution state easily and immediately at the sight of a displayed distribution diagram.

The present invention provides a particle analyzer comprising a detection section to detect a parameter representative of characteristics of particles in a sample, a processing section to process the detected parameter and an output section to output a result obtained by the processing section, wherein the processing section includes a distribution diagram producing section to produce a distribution diagram based on the parameter detected by the detection section, an area storing section to store a predetermined reference pattern beforehand and a control section to permit the output section to output the reference pattern in addition to the distribution diagram.

BRIEF DESCRIPTION OF THE DRAWINGS

For a further understanding of the nature and objects of the present invention, reference should be made to the following detailed description taken in conjunction with the accompanying drawings, wherein.

DESCRIPTION OF THE PREFERRED EMBODIMENTS

The particles analyzed in the present invention are substances contained in fluid such as blood and urine of mammals including human beings, the substances including erythrocytes, leukocytes, epithelial cells and casts, for example. The detection section to detect a parameter representative of characteristics of particles may be a known detector such as an optical detector and an electric detector. In the optical detector, a liquid sample containing particles to be analyzed is passed in a sheath flow cell and irradiated with light, and then a light signal such as transmitted light, scattered light, fluorescent light or the like is detected as a parameter. In the electric detector, a liquid sample containing particles to be analyzed is passed through an orifice, and a change in electric resistance or impedance in the orifice caused by the particles is detected as a parameter.

The processing section to process the detected parameter may be composed of a microcomputer or a personal computer.

The output section to output the result obtained by the processing section may be a display device such as CRT and LCD or a printer such as a laser printer.

Examples of the distribution diagrams produced by the distribution diagram production section of the processing section are a one-dimensional frequency distribution graph (histogram), a two-dimensional scattergram and a three-dimensional scattergram. Examples of the reference patterns pre-stored in the area storing section, in the case of analyzing blood cells, include those showing specific areas in histograms of leukocytes (WBC), eosinophils (EO), basophils (BASO) and the like, e.g., a normal specimen pattern and an abnormal specimen pattern showing areas in which cells of a normal specimen and cells of an abnormal specimen are distributed, respectively, and those showing specific areas in multi-dimensional scattergrams of lymphocytes, monocytes, granulocytes and the like in leukocytes, particularly a normal specimen pattern and an abnormal specimen pattern showing areas in which cells of a normal specimen and cells of an abnormal specimen appear, respectively.

In this connection, the reference pattern pre-stored in the area storing section is preferably established statistically by analyzing through this analyzer a large number of normal specimens and abnormal specimens which have been microscopically determined.

The analyzer of the invention may be provided with an input means such as a keyboard and a mouse for giving instructions about processing conditions in the processing section. The control section can control the output section to output the reference pattern pre-stored in the area storing section in addition to the distribution diagram of the analyzed sample. In this case, the analyzer is preferably so constructed that the reference pattern added to the distribution diagram of the measured particles can be selected according to an instruction from the input means. In other words, the analyzer is preferably adapted to be selectively switched between a reference pattern off mode (the first mode) in which the distribution diagram is outputted without the reference pattern and a reference pattern add-on mode (the second mode) in which the distribution diagram is outputted with the reference pattern. Further, it is preferred that the analyzer is provided with a plurality of reference patterns such as the normal specimen pattern and the abnormal specimen pattern as described above so that the analyzer has various modes such as a normal specimen pattern add-on mode and an abnormal specimen pattern add-on mode.

The control section may also have a function of permitting the output section to output enlarged and reduced distribution graphs and reference patterns in accordance with an instruction from the input section.

A feature of the present invention is to simultaneously output the distribution diagram and the reference pattern through the output section, thereby to enable a user to form judgment on the distribution state of the distribution diagram immediately and easily at sight by referencing the reference pattern. Additionally, if the user feels the reference pattern add-on mode inconvenient, the reference pattern turn-off mode can be selected.

EXAMPLE 1

Figure 1:
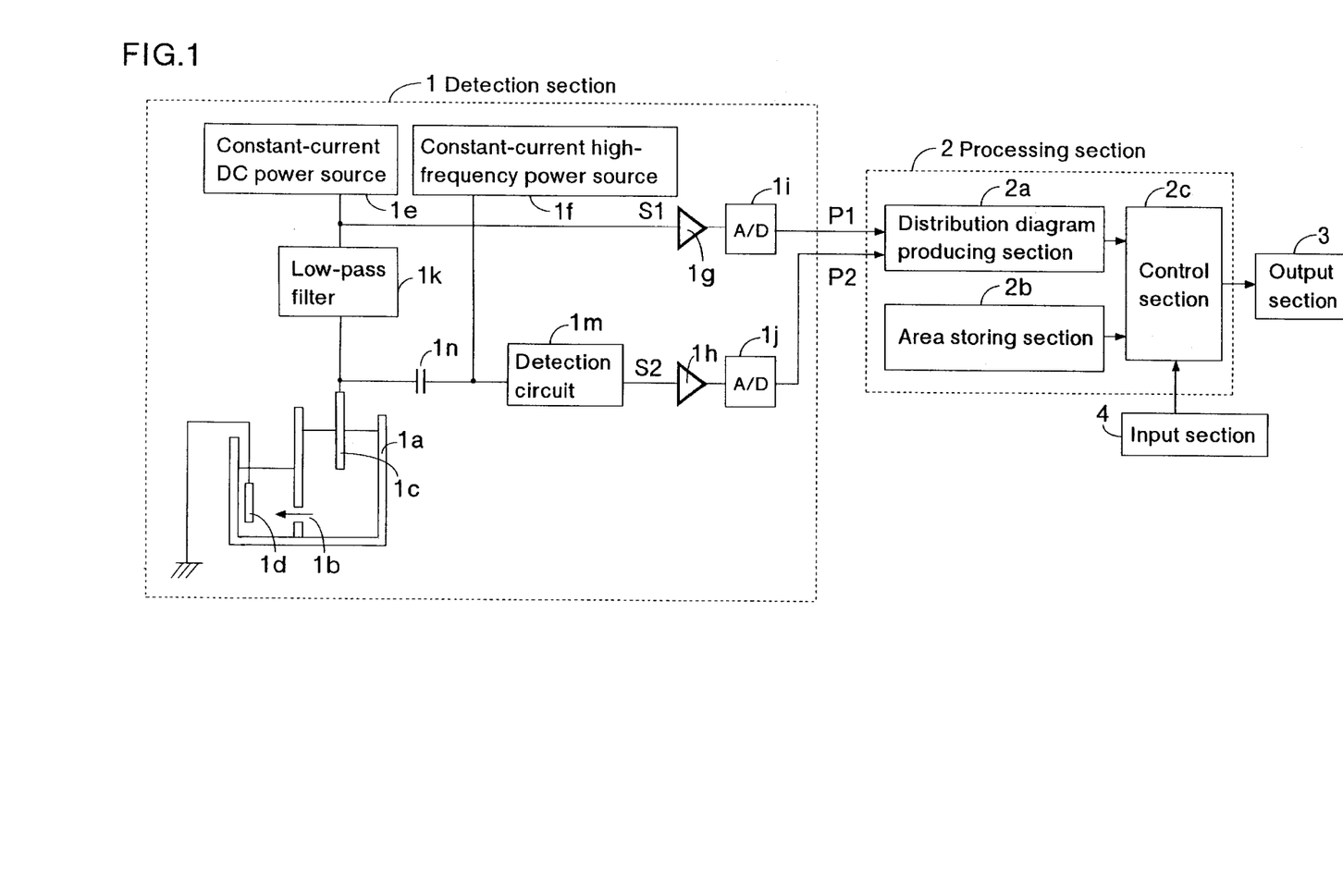
FIG. 1 is a diagram illustrating the construction of an apparatus in accordance with Example 1 of the present invention.

This example is a blood analyzer of the present invention, which has a detection section 1 as shown in FIG. 1. The detection section 1 determines individual blood cells in a suspension sample which has been subjected to pretreatment such as dilution and hemolysis for analysis. The detection section 1 individually detects blood cells to determine plural kinds of parameters for each blood cell.

In the detection section 1, the suspension is put in a chamber $1a$. Direct current and alternating current are simultaneously supplied to an orifice $1b$ of the chamber $1a$ from a constant-current DC power source $1e$ and a constant-current high-frequency power source $1f$ via electrodes $1c$ and $1d$. Individual blood cells are passed through the orifice $1b$. For each blood cell passing, the detection section detects a signal based on change of resistance and a signal based on change of impedance. When the direct current is being supplied to the orifice $1b$, a signal S1 is obtained which is proportional to the size of cytoplasm of a cell which passes through the orifice $1b$.

When the high-frequency current is being supplied to the orifice $1b$, a signal S2 is obtained which is integrally representative of both the density and the size of a nucleus and granules of a cell which passes through the orifice $1b$ because the impedance becomes small for a low-density substance like a blood cell and cytoplasm and it becomes large for a high-density substance like a nucleus and a granule.

A low-pass filter $1k$ removes a high-frequency component from a voltage applied across the electrodes $1c$ and $1d$ for the purpose of detecting only a direct-current component therefrom to obtain a signal S1. On the other hand, a condenser in removes the direct-current component from the voltage applied across the electrodes $1c$ and $1d$ for the purpose of obtaining only the alternating-current component. A detecting circuit $1m$ detects the alternating-current component of the voltage applied across the electrodes $1c$ and $1d$ to obtain a signal S2.

The two signals S1 and S2 are amplified by amplifiers $1g$ and $1h$ and then converted to parameters P1 and P2 in the form of a digital signal by A/D converters $1i$ and $1j$, respectively. In other words, the signals are quantized.

By this quantization, the parameter P1 representing the size of cytoplasm of a blood cell is classified into one of 256 channels from 0 to 255 (referred to an i channel hereafter). Similarly, the parameter P2 integrally representing both the density and size of the nucleus and granules of the blood cell is classified into one of 256 channels from 0 to 255 (referred to a j channel hereafter).

The parameters P1 and P2 are supplied to a processing section 2. The processing section 2 is composed of a personal computer or a micro computer to which an output section 3 and an input section 4 are connected. Here, a CRT is used as the output section 3 and a keyboard is used as the input section 4.

Figure 22:
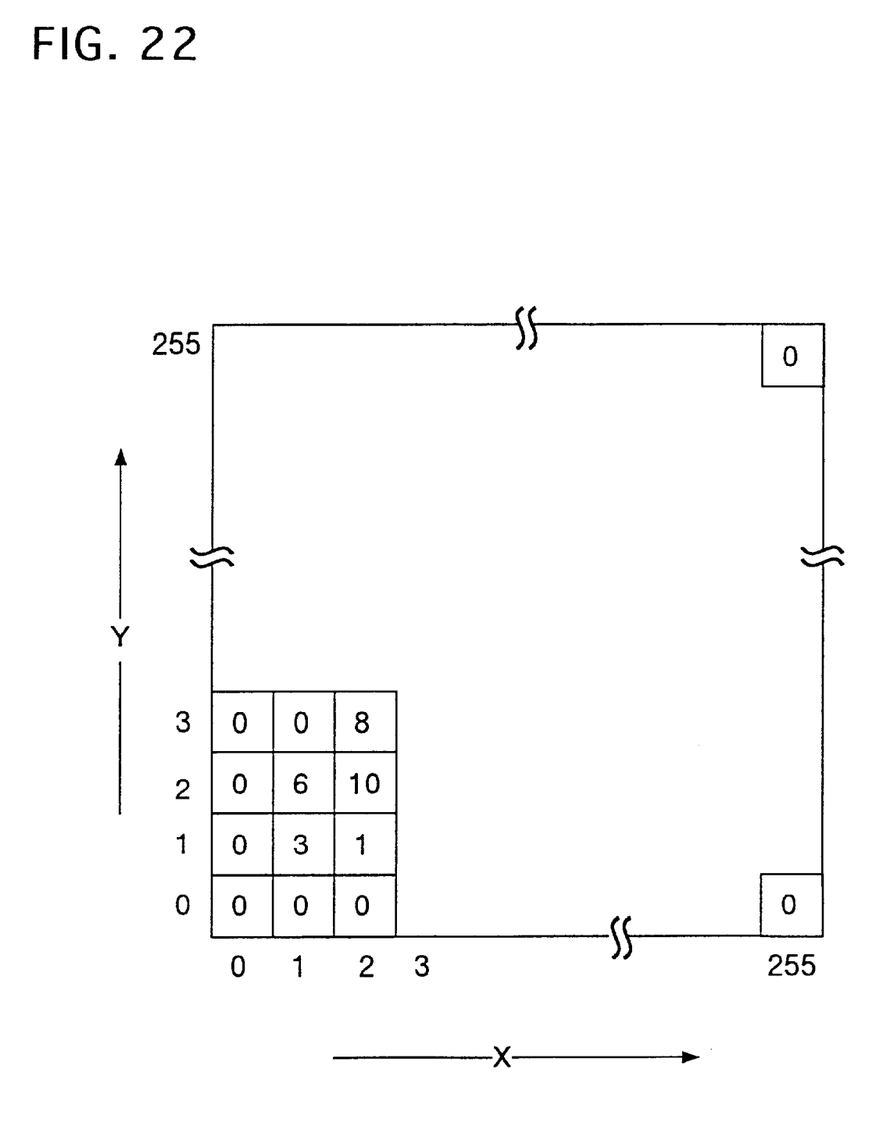
FIG. 22 illustrates a coordinate system for the distribution diagram in accordance with Example 1.

In the processing section 2, a distribution diagram producing section $2a$, based on the parameters P1 and P2, produces a distribution diagram with the i channel and the j channel plotted in abscissa (X-axis) and ordinate (Y-axis), respectively, as shown in FIG. 22, for the classification of leukocytes into lymphocytes, monocytes and granulocytes and the like.

Since each of the ordinate and the abscissa have 256 channels, the distribution diagram is composed of 256×256 grids each representing a state of a blood cell. Each of the grids stores the number of blood cells having the state corresponding to the grid. For example, supposing the value stored in the grid defined by 1 channel in abscissa and 2 channel in ordinate is six, six blood cells exist whose parameters P1 representative of the size of cell cytoplasm are 1 and whose parameters P2 integrally representative of the density and size of their nuclei and granules are 2.

Figure 2:
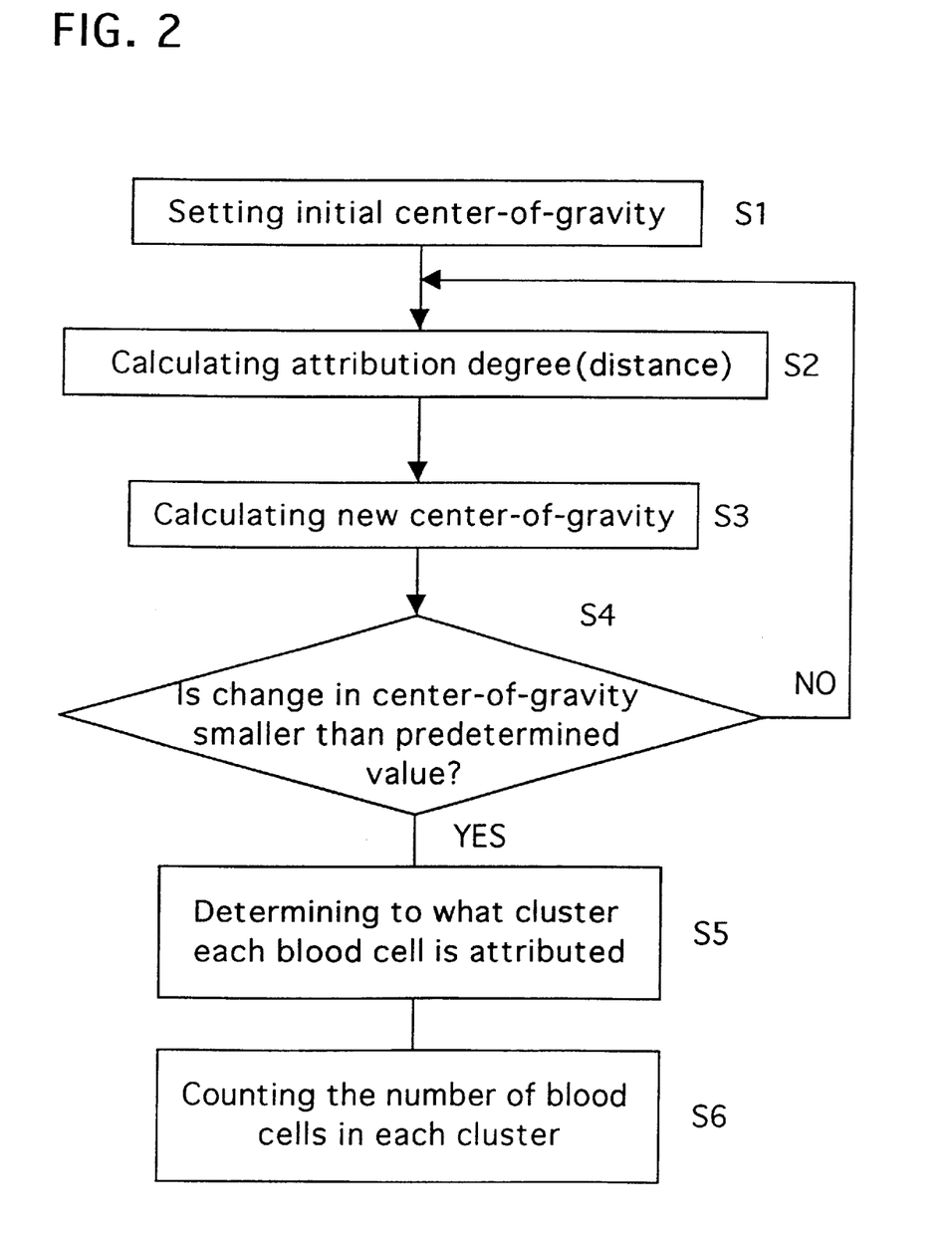
FIG. 2 is a flowchart illustrating a part of operation in accordance with Example 1.

Based on this distribution diagram data, the distribution diagram producing section $2a$ performs an operation as shown in a flowchart of FIG. 2 to classify and count the blood cells.

An center-of-gravity, i.e., an initial center-of-gravity, of each cluster such as lymphocytes, granulocytes, monocytes and the like is set in the distribution diagram data beforehand (Step 1). For each of the blood cells, the distances between the grid of the blood cell and the grids of the centers-of-gravity of the individual clusters are calculated. When the distance between the blood cell and the center-of-gravity of a certain cluster is the smallest of all the calculated distances about that blood cell, the attribution degree of the blood cell to that cluster is set to 1. The attribution degrees of the blood cell to the other clusters are set to 0. Thus the attribution degrees of all the blood cells to each of the clusters are determined (Step S2).

Next, assuming that all the blood cells belong to one of the clusters according to their attribution degrees, a new center-of-gravity is determined for each of the clusters (Step S3) including the examined blood cells. If difference between the prior center-of-gravity and the present center-of-gravity is not smaller than a predetermined value (Step 4), Steps 2 and 3 are repeated until the difference between a present center-of-gravity and a prior center-of-gravity becomes smaller than the predetermined value. When the difference becomes smaller than the predetermined value, the attribution of each of the blood cells is determined depending on the present attribution degrees of the blood cell to the individual clusters (Steps S4 and S5). The number of blood cells belonging to the individual clusters is calculilated (Step S6).

Further, the processing section 2 is provided with an area storing section 2b to store area patterns in accordance with the coordinate system of the distribution diagram. The area pattern is outputted with the distribution diagram by the output section 3 for judging that blood cells appearing in an area shown by the area pattern are normal or abnormal. The area pattern assists a user in judging from the distribution diagram immediately and easily when the user sees the distribution diagram outputted by the output section 3.

A. Analysis of Lymphocytes, Monocytes and Granulocytes in Leukocytes

A blood sample is diluted and erythrocytes therein are simultaneously lysed with a reagent for classifying leukocytes . Then the sample is put into the chamber 1a of the apparatus shown in FIG. 1 for analysis.

Figure 4:
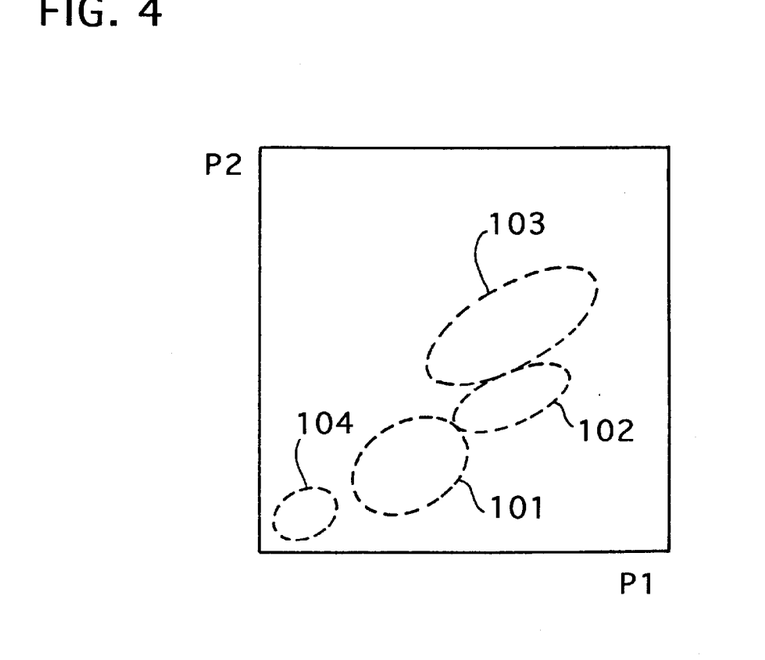
FIG. 4 illustrates area patterns in accordance with Example 1.
Figure 5:
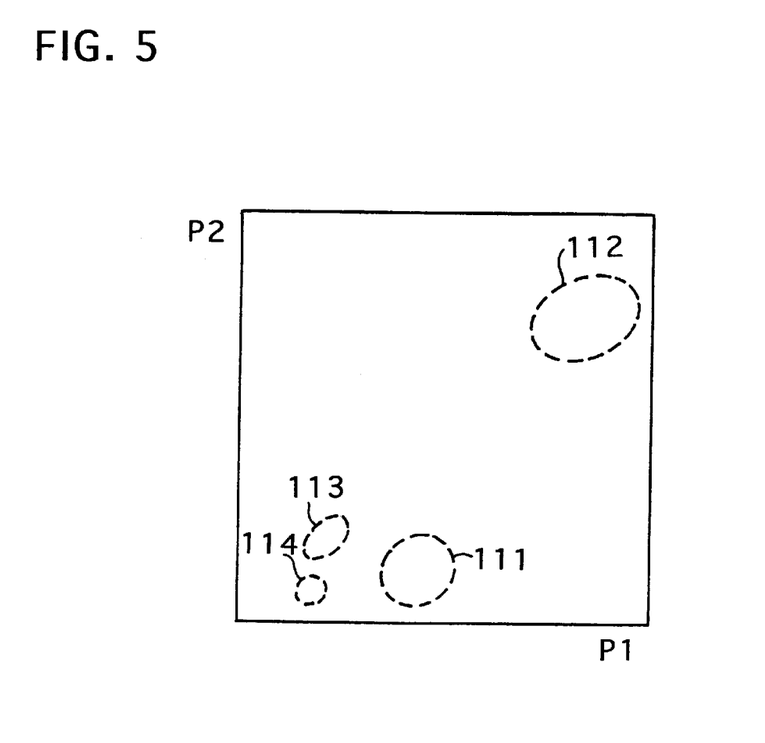
FIG. 5 illustrates area patterns in accordance with Example 1.

In this case, the area storing section 2b pre-stores area patterns showing areas 101, 102, 103 and 104 in which lymphocytes, monocytes, granulocytes and ghost of normal specimens appear, respectively (normal specimen patterns) as well as area patterns showing areas 111, 112, 113 and 114 in which "atypical lymphocytes and blasts," "immature granulo-cytes," "platelet aggregation" and "nuclear erythrocytes" of abnormal specimens appear, respectively (abnormal specimen pattern).

Figure 6:
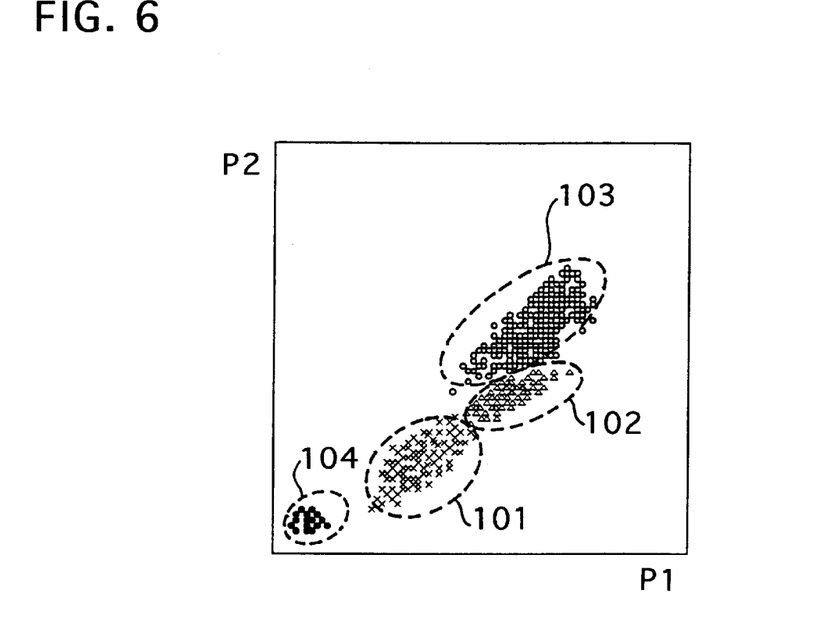
FIG. 6 is an exemplary distribution diagram outputted in accordance with Example 1.

The user operates a predetermined key provided in the input section 4 to select a reference pattern off mode, a normal specimen pattern add-on mode and an abnormal specimen pattern add-on mode. When the normal specimen pattern addonmode is selected, the output section 3 outputs the distribution diagram of the examined sample produced by the distribution diagram producing section 2a together with the normal specimen pattern, as shown in FIG. 6. Here, X, Δ, ○ and a black ● denote a lymphocyte, a monocyte, a granulocyte and a ghost, respectively. These respective clusters exist within the area patterns 101, 102, 103 and 104. Accordingly, the user can immediately find from FIG. 6 that the lymphocytes, monocytes and granulocytes of this sample are normal.

Figure 7:
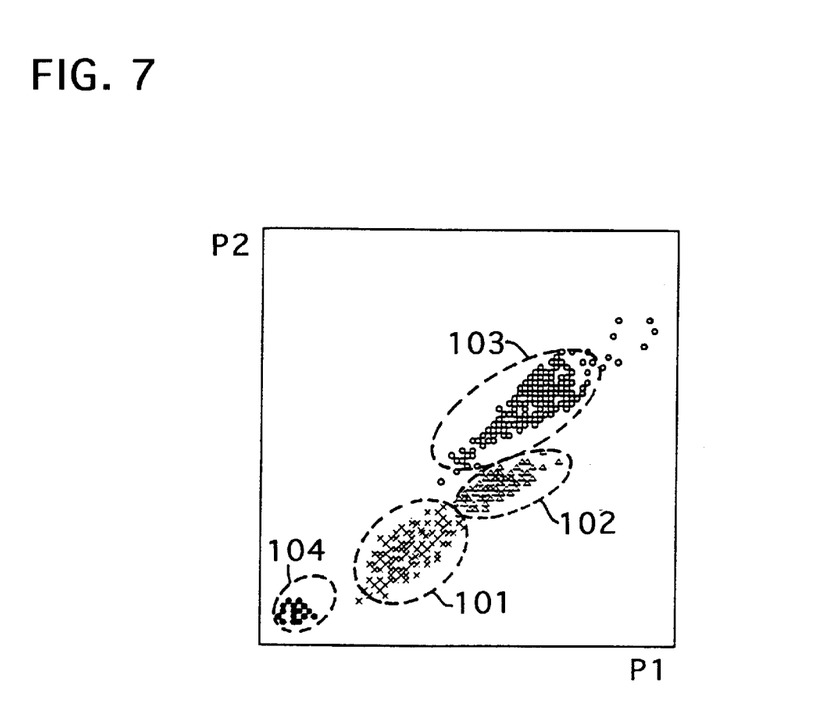
FIG. 7 is an exemplary distribution diagram outputted in accordance with Example 1.

Next, another blood sample is diluted and erythrocytes are lysed in the same manner as described above. Then the sample is put into the chamber 1a of the apparatus shown in FIG. 1 for analysis. When the user operates the input section 4 as described above, the output section 3 outputs a distribution diagram shown in FIG. 7.

Figure 8:
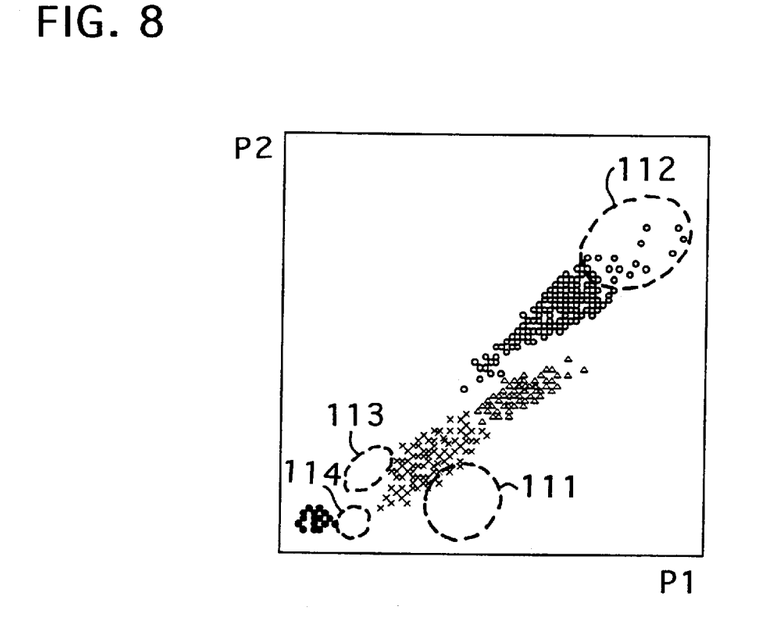
FIG. 8 is an exemplary distribution diagram outputted in accordance with Example 1.

The user can change modes from the normal specimen pattern add-on mode to the abnormal specimen pattern add-on mode by key operation as necessary. In this case, the abnormal specimen pattern is outputted together with the distribution diagram of the examined sample by the output section 3. The user can immediately find that this sample is an abnormal one containing "immature granulocytes" since blood cells exist within the area pattern 112.

Figure 9:
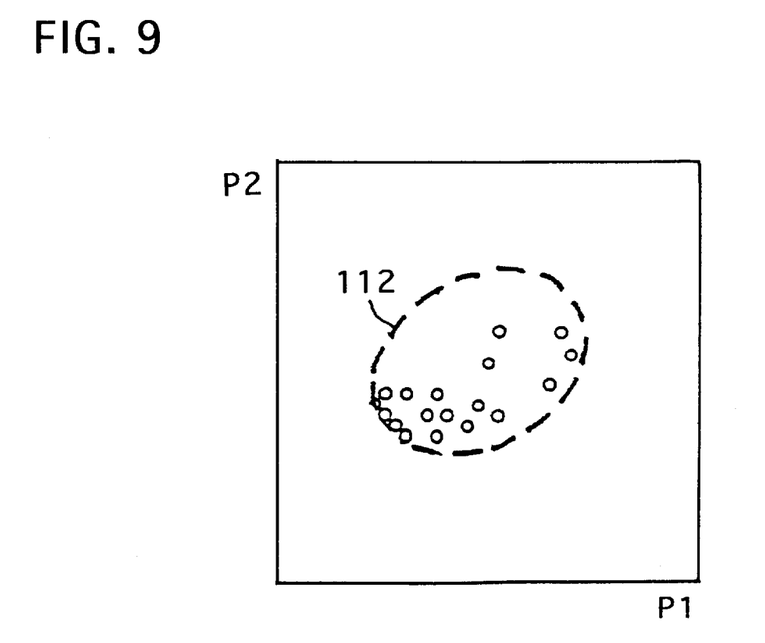
FIG. 9 is an exemplary distribution diagram outputted in accordance with Example 1.
Figure 10:
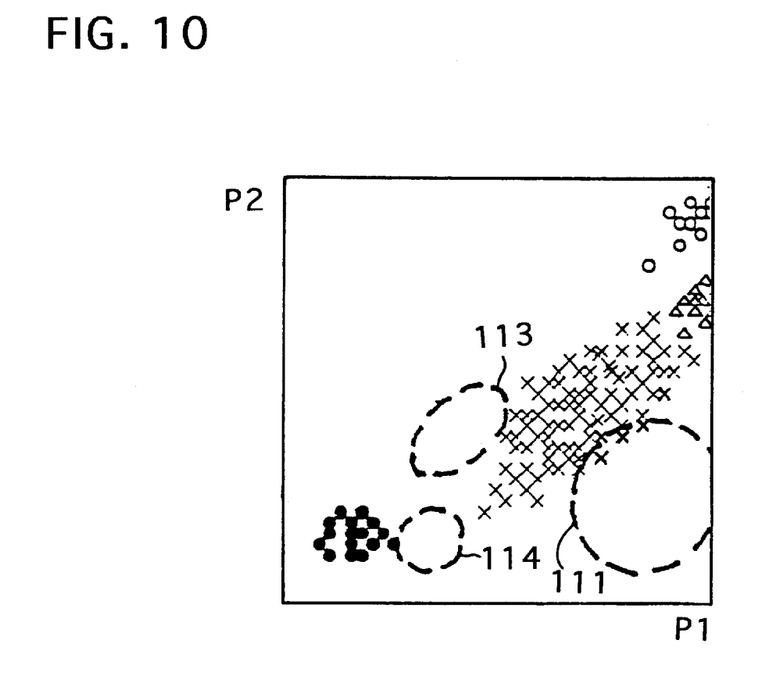
FIG. 10 is an exemplary distribution diagram outputted in accordance with Example 1.

At this time, the user can enlarge and output essential parts of FIG. 8 through the output section 3 as shown in FIGS. 9 and 10 by further operating the input section 4.

B. Analysis of Juvenile Leukocytes

A blood sample is diluted with a reagent for analyzing juvenile leukocytes to lyse erythrocytes, denude nuclei of and shrink other leukocytes than juvenile leukocytes. Then the sample is put into the chamber 1a of the apparatus shown in FIG. 1 for analysis. In this case, the area storing section 2b pre-stores an area pattern 105 in which "ghosts" of normal specimens appear as shown in FIG. 11 as well as area patterns 115, 116, 117 and 118 in which "blasts," "immature granulocytes," "left shift," and "platelet clumps" appear, respectively.

Figure 11:
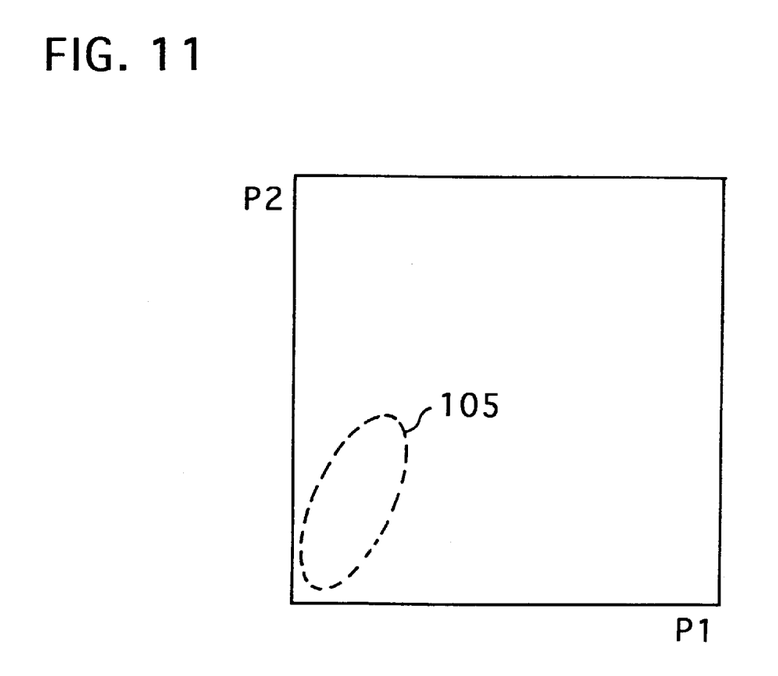
FIG. 11 illustrates an area pattern in accordance with Example 1.
Figure 13:
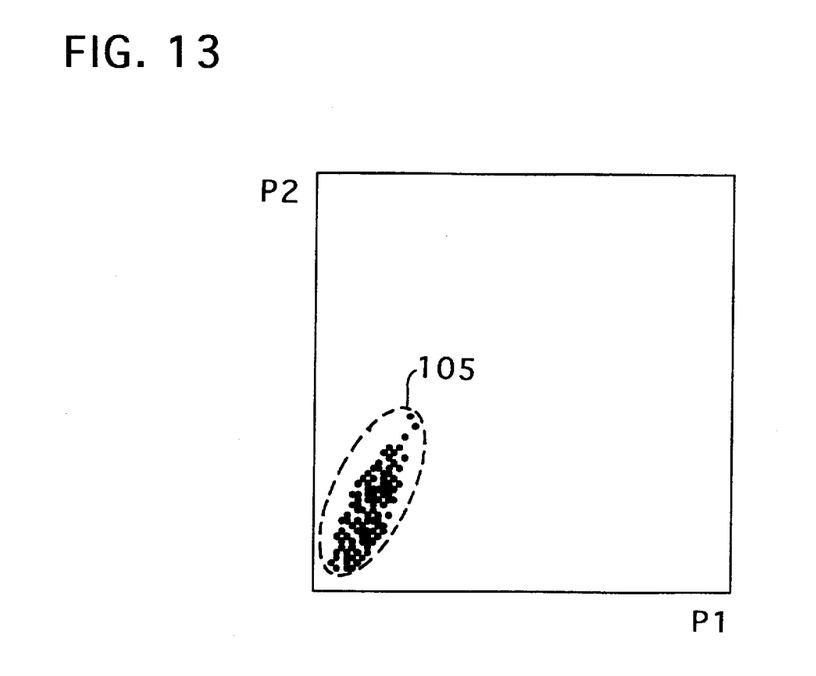
FIG. 13 is an exemplary distribution diagram outputted in accordance with Example 1.

When the user operates the input section 4 to select an area pattern as shown in FIG. 11, the output section 3 outputs a distribution diagram as shown in FIG. 13, in which a black ● denotes a ghost. Since a mass exists within the area pattern 105 in FIG. 13, the user can immediately find that this sample does not contain juvenile cells and is normal.

Figure 12:
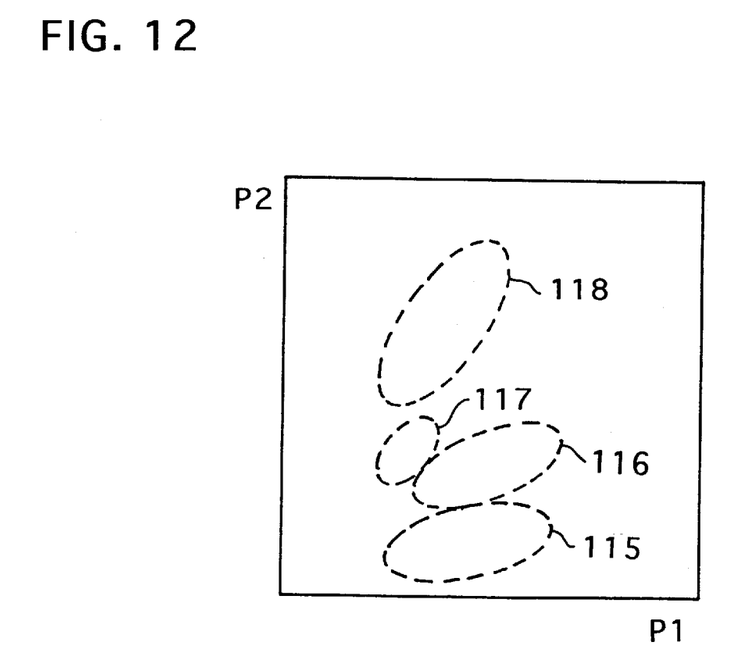
FIG. 12 illustrates area patterns in accordance with Example 1.
Figure 14:
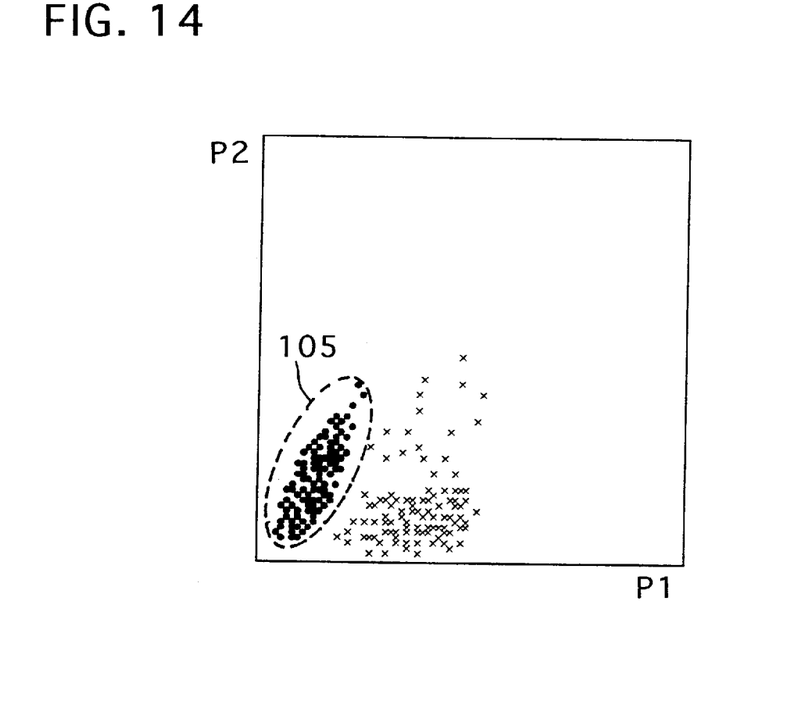
FIG. 14 is an exemplary distribution diagram outputted in accordance with Example 1.

Next, erythrocytes of another blood sample are lysed, nuclei of other leukocytes than juvenile cells are denuded and these other leukocytes are shrunk. Then, the sample is put into the chamber 1a of the apparatus shown in FIG. 1. The output section outputs a distribution diagram as shown in FIG. 14. When the user recognizes the distribution extends out of the area pattern 105, the user further operates the input section 4 to output an area pattern shown in FIG. 12 together with the distribution diagram. The distribution diagram shown in FIG. 15 is obtained.

Figure 15:
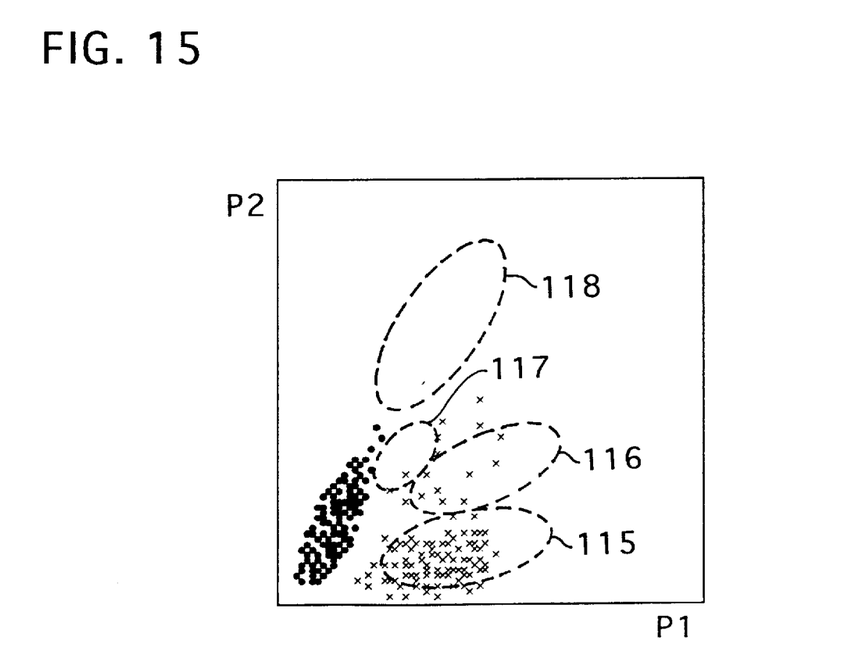
FIG. 15 is an exemplary distribution diagram outputted in accordance with Example 1.

The user can immediately recognize from FIG. 15 that this sample is an abnormal one which contains "blasts," "immature granulocytes" and "left shift."

EXAMPLE 2

Figure 3:
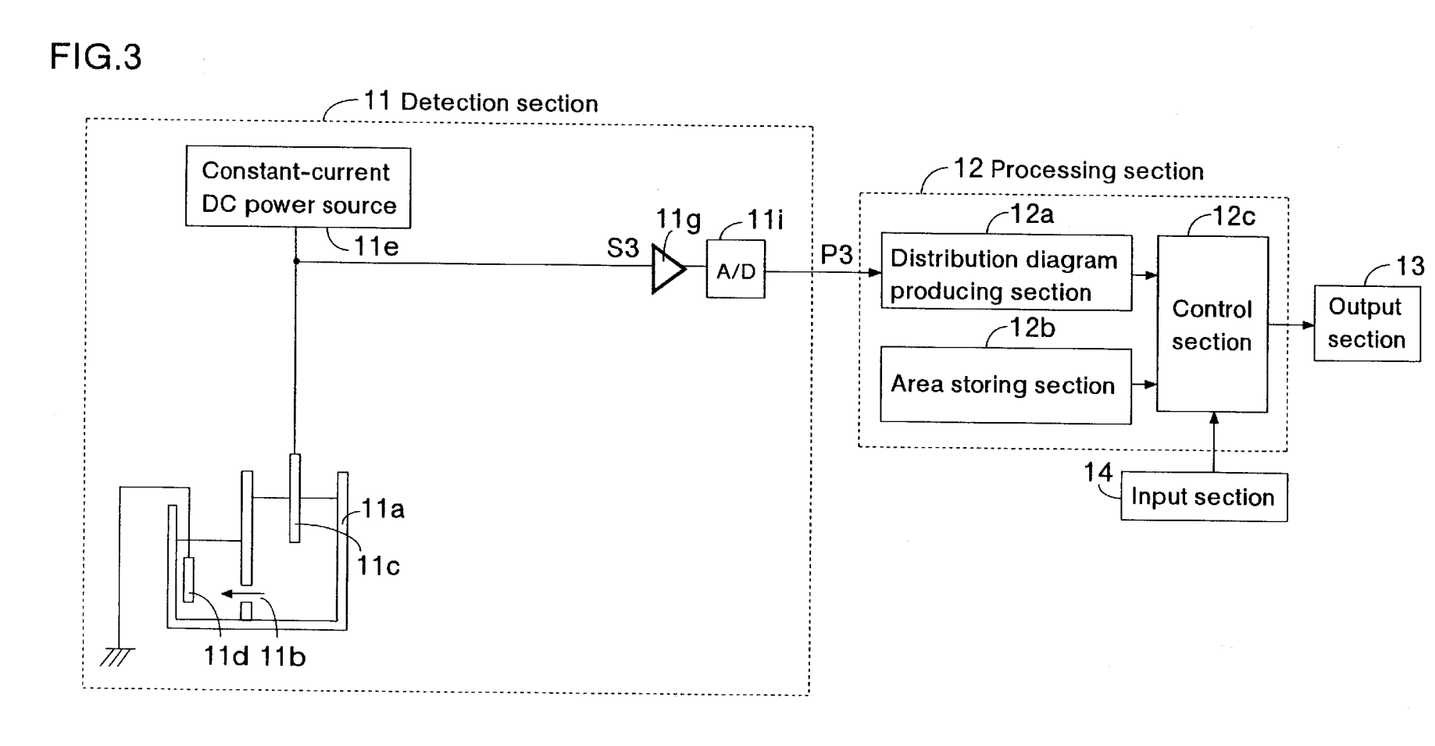
FIG. 3 is a diagram illustrating the construction of an apparatus in accordance with Example 2 of the present invention.

This example is another blood analyzer of the invention, which is provided with a detection section 11 as shown in FIG. 3. The detection section 11 analyzes blood cells in a suspension sample.

In the detection section 11, the suspension is put into a chamber 11a. Direct current is supplied to an orifice 11b of the chamber 11a from a constant-current DC power source 11e through electrodes 11c and 11d. When a blood cell passes through the orifice 11b, a signal S3 proportional to the size of the cytoplasm of the blood cell is obtained. The signal S3 is amplified by an amplifier 11g and then converted to a parameter P3 in the form of a digital signal, i.e., quantized, by an A/D converter 11i.

The parameter P3 is supplied to a processing section 12. Here, the processing section 12 is composed of a personal computer or a micro computer. As an output section 13 and an input section 14 connected to the processing section 12, used are a CRT and a keyboard, respectively.

In the processing section 12, a distribution diagram producing section 12a produces one-dimensional frequency distribution diagrams based on the parameter P3.

Patterns are pre-stored in an area storing section 12b, which patterns are in accordance with the coordinate system for the distribution diagrams. The pattern is outputted with the distribution diagram by the output section 13 for judging whether blood cells appearing in an area shown in the pattern are normal or abnormal. The pattern assists a user in judging from the distribution diagram immediately and easily when the user sees the distribution diagram outputted by the output section 13.

A. Analysis of the Number of Leukocytes

A blood sample is diluted with a reagent for counting the number of leukocytes to lyse erythrocytes and shrink platelets. Then the sample is put into the chamber 11a of the apparatus shown in FIG. 3.

Figure 16:
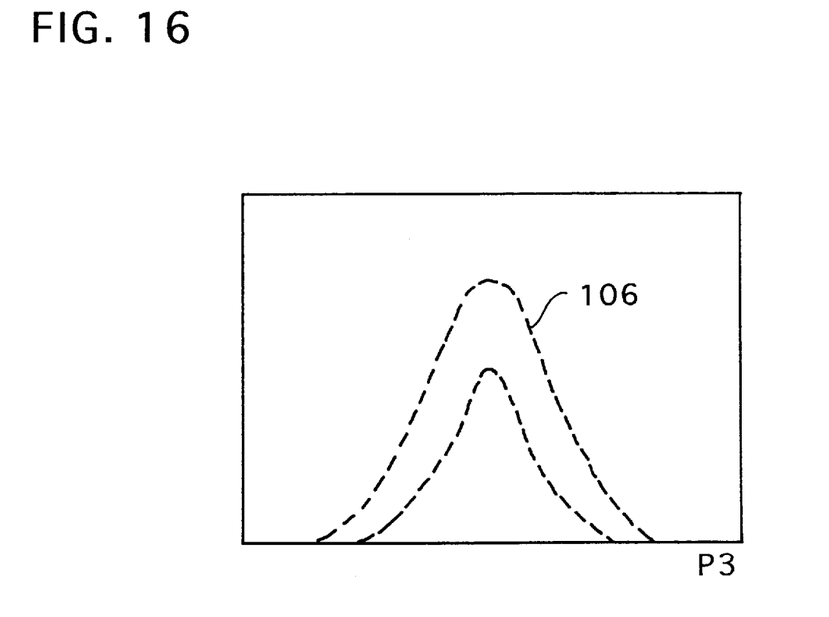
FIG. 16 illustrates an area pattern in accordance with Example 2.

In this case, a reference pattern 106 as shown in FIG. 16 which shows a particle size distribution of leukocytes of normal specimens is stored beforehand in the area storing section 12b.

The user operates the input section 14 to output the pattern 106 together with the frequency distribution diagram produced by the distribution diagram producing section 12a by the output section 13. The output section 13 outputs a distribution diagram as shown in FIG. 17 or 18.

Figure 17:
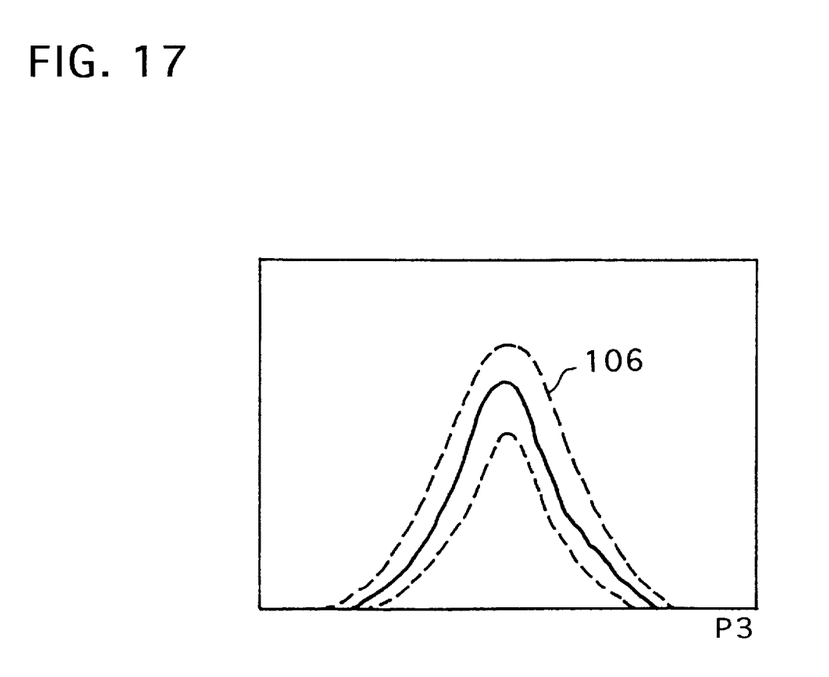
FIG. 17 is an exemplary distribution diagram outputted in accordance with Example 2.
Figure 18:
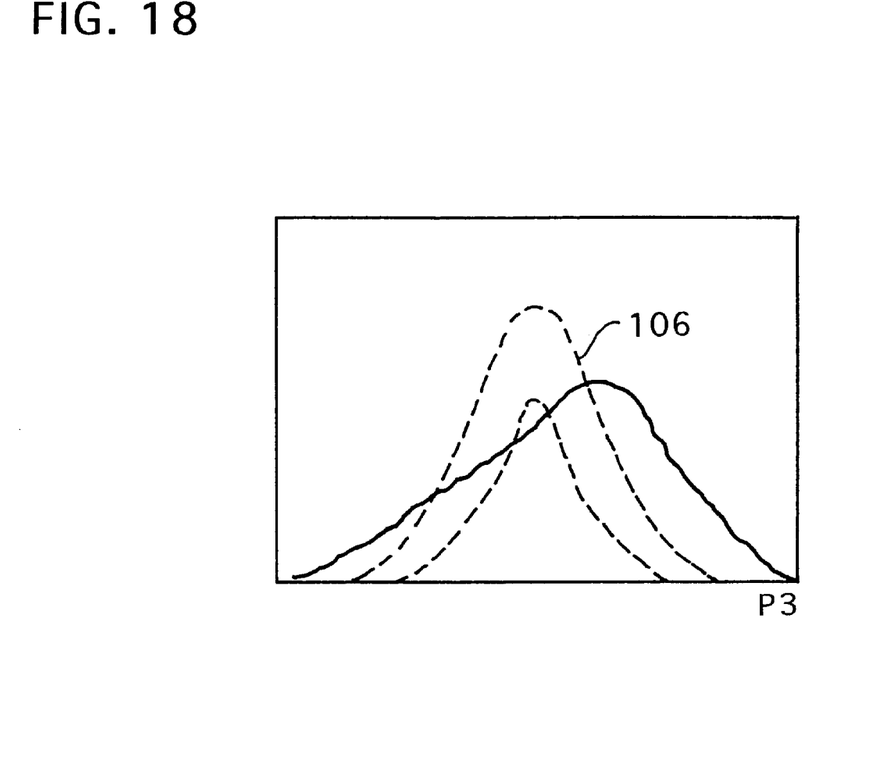
FIG. 18 is an exemplary distribution diagram outputted in accordance with Example 2.

When the user obtains a distribution diagram as shown in FIG. 17, the user can immediately find that the sample has a normally distributed particle size of leukocytes because the particle size distribution curve is within the reference pattern 106. When the user obtains a distribution diagram as shown in FIG. 18, on the other hand, the user can immediately find that the sample has an abnormally distributed particle size of leukocytes because the particle size distribution curve extends out of the reference pattern 106.

B. Analysis of Basophils in Blood

A blood sample is diluted with a reagent for analyzing basophils to lyse erythrocytes, denude nuclei of other leukocytes other than basophils and to shrink these other leukocytes. Then the sample is put into the chamber 11a of the apparatus shown in FIG. 3 for analysis.

Figure 19:
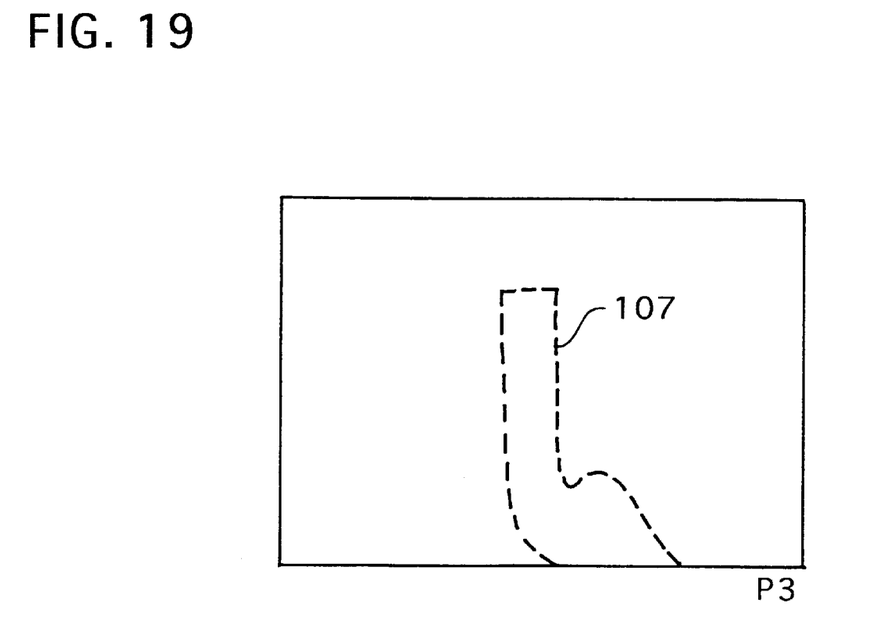
FIG. 19 illustrates an area pattern in accordance with Example 2.

In this case, a reference pattern 107 as shown in FIG. 19 is pre-stored in the area storing section 12b, which reference pattern shows particle size distribution of basophils of normal specimens.

The user operates the input section 14 to output the reference pattern 107 together with the frequency distribution diagram produced by the distribution diagram producing section 12a by the output section 13. The output section 13 outputs a distribution diagram as shown in FIG. 20 or 21.

Figure 20:
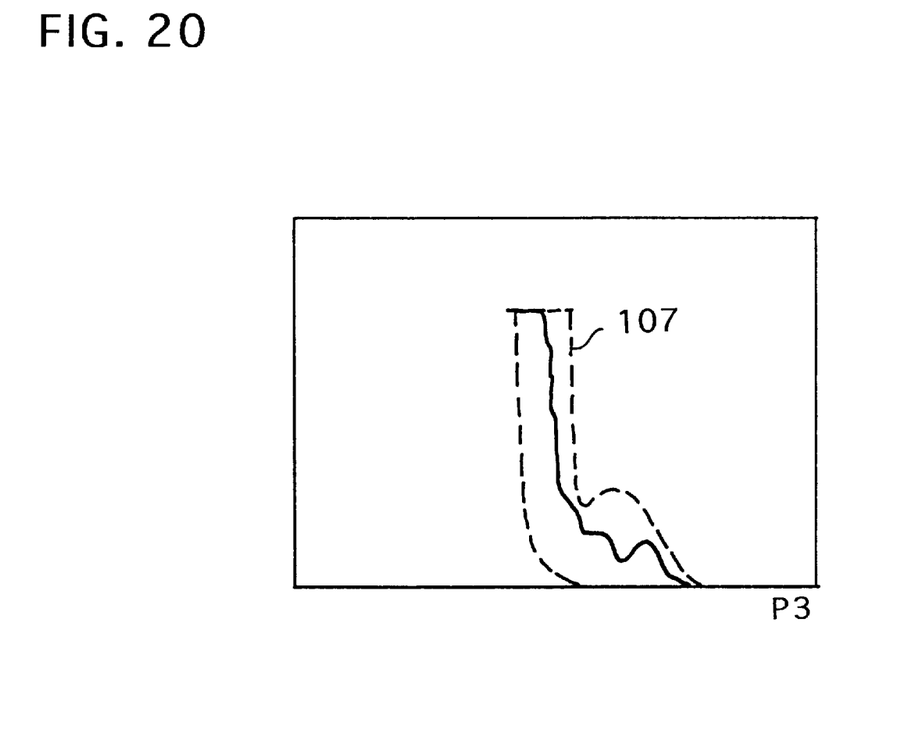
FIG. 20 is an exemplary distribution diagram outputted in accordance with Example 2.
Figure 21:
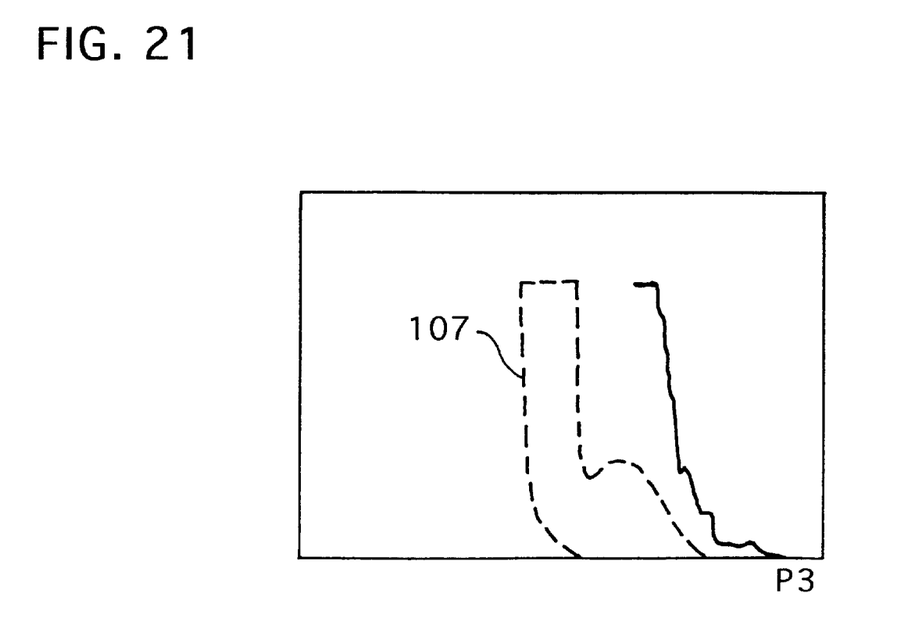
FIG. 21 is an exemplary distribution diagram outputted in accordance with Example 2.

When the user obtains a distribution diagram as shown in FIG. 20, the user can immediately find that the sample has a normally distributed particle size of basophils because the particle size distribution curve is within the reference pattern 107. When the user obtains a distribution diagram as shown in FIG. 21, the user can immediately find that the sample has an abnormally distributed particle size of basophils because the particle size distribution curve extends out of the reference pattern 107.

According to the present invention, a distribution diagram of an examined sample can be outputted together with a reference pattern having a predetermined meaning. Thereby, the distribution state of the distribution diagram is easily and immediately judged using the reference pattern as an indicator.

What is claimed is:

1. A particle analyzer comprising:
    a detection section to detect a parameter representative of characteristics of particles in a sample;
    a processing section to process the detected parameter;
    a display section to display a result obtained by the processing section, wherein the processing section produces a scattergram based on the parameter detected, stores a plurality of predetermined normal specimen reference patterns, each of which is defined by a closed curve, and controls the display section to simultaneously display both a closed curve defining at least one of the predetermined normal specimen reference patterns and the scattergram of the detected parameter, the closed curve being superimposed over the scattergram so as to enable a user to form an on-sight comparison between said scattergram and said closed curve of said at least one reference pattern to determine whether the detected parameter is abnormal or not; and
    an input section to direct said processing section to select said at least one of the predetermined normal specimen reference patterns for display of its corresponding closed curve by said display section.

2. The particle analyzer of claim 1,
    wherein said input section selectively instructs said display section to display the scattergram without the closed curve of said selected reference pattern or to display the scattergram together with the closed curve of said selected reference pattern.

3. The particle analyzer of claim 1,
    wherein said input section instructs said processing section about size of the scattergram and said selected reference pattern, and
    wherein said processing section controls said display section to display both the scattergram and the closed curve of said selected reference pattern in the size instructed by said input section.

4. The particle analyzer of claim 1,
    wherein said input section instructs said processing section about desired parts of the scattergram and said selected reference pattern, and
    wherein the control section further has a function of permitting the display section to display the desired parts of the scattergram and the closed curve of said selected reference pattern.

5. The particle analyzer of claim 1, wherein the scattergram is a multidimensional scattergram.

6. The particle analyzer of claim 1, wherein the normal specimen pattern shows at least one area in which leukocytes, monocytes, granulocytes or ghost of normal specimens appear, and the abnormal specimen pattern shows at least one area in which blasts, immature granulocytes, left shift or platelet clumps of abnormal specimens appear.

7. The particle analyzer of claim 1, wherein the scattergram includes at least one of multidimensional scattergrams of lymphocytes, monocytes and granulocytes.

8. The particle analyzer of claim 1, wherein the detection section includes an electric detector.

9. The particle analyzer of claim 8, wherein the electric detector receives a liquid sample containing particles to be analyzed through an orifice, and a change in electric resistance or impedance due to the particles passing through the orifice is detected as the parameter.

10. The particle analyzer of claim 1, wherein the detection section includes an optical detector.

11. The particle analyzer of claim 10, wherein the optical detector receives a liquid sample containing particles to be analyzed in a sheath flow cell and irradiated with light, and wherein one of at least transmitted light, scattered light and fluorescent light is detected as the parameter.

12. The particle analyzer of claim 1, wherein the predetermined specimen reference pattern is at least one of a normal specimen pattern and an abnormal specimen pattern; and, wherein the particle analyzer further comprises a means for selecting between the normal specimen pattern and an abnormal specimen pattern.

13. A method of analyzing a particle, comprising:

selecting one from a plurality of predetermined reference patterns detecting a parameter representative of characteristics of particles in a sample;

processing the parameter; and displaying a result obtained by the step of processing, wherein the result is a simultaneous display of both a scattergram based on the parameter, and said selected predetermined reference pattern defined by a closed curve, the closed curve being superimposed over the scattergram to enable a user to form an on-sight comparison between said scattergram and said closed curve of said reference pattern to determine whether the detected parameter is abnormal or not.

14. The method according to claim 13, wherein said predetermined reference pattern is at least one of a normal specimen pattern and an abnormal specimen pattern, and wherein said step of selecting further includes selecting between a normal specimen pattern and an abnormal specimen pattern.

* * * * *